United States Patent [19]
Yano et al.

[11] Patent Number: 5,643,793
[45] Date of Patent: Jul. 1, 1997

[54] METHOD FOR PRODUCING OPTICALLY ACTIVE 3-HYDROXYHEXANOIC ACIDS USING PORCINE PANCREATIC LIPASE

[75] Inventors: Hitoshi Yano; Naoyuki Yoshida; Teruyo Sugiura, all of Ichihara, Japan

[73] Assignee: Chisso Corporation, Osaka, Japan

[21] Appl. No.: 542,067

[22] Filed: Oct. 12, 1995

[30] Foreign Application Priority Data

Oct. 17, 1994 [JP] Japan .................... 6-277130

[51] Int. Cl.[6] .................................. C12P 41/00
[52] U.S. Cl. ............................................. 435/280
[58] Field of Search ................................. 435/280

[56] References Cited

U.S. PATENT DOCUMENTS 5,128,252  7/1992  Miyazawa et al. ............... 435/134

OTHER PUBLICATIONS

Sigma Catalog p. 611 (1992).
Bornscheuer U., Tetrahedron: Assymetry 4(5): 1007–1016 (1993).
Cambou B., Biotech. Bioengin. XXVI : 1449–54 (1984).

Primary Examiner—David M. Naff
Assistant Examiner—S. Saucier
Attorney, Agent, or Firm—Wenderoth, Lind & Ponack

[57] ABSTRACT

A method for producing an optically active 3-hydroxyhexanoic acid represented by formula (1) and the enantimer by asymmetrically hydrolyzing a racemic ester of 3-hydroxyhexanoic acid in the presence of a lipase derived from porcine pancreas.

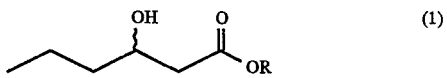

(1)

6 Claims, No Drawings

METHOD FOR PRODUCING OPTICALLY ACTIVE 3-HYDROXYHEXANOIC ACIDS USING PORCINE PANCREATIC LIPASE

BACKGROUND OF THE INVENTION

1. Field of the Invention

The present invention relates to a method for producing optically active 3-hydroxyhexanoic acids useful as intermediates for synthesizing medicine and agricultural chemicals.

2. Description of the Prior Art

Lately, it has become important to synthesize physiologically active substances as optically active compounds. In a physiologically active substance having several kinds of optical isomers, these isomers often show a difference in activity. Among these isomers, one isomer has strong activity and the other isomers show weak activity or undesired toxicity. Accordingly, when the physiologically active substances are synthesized, it is desired to selectively synthesize preferable optical isomers not only to develop full physiological activity but also in safety.

Hitherto, as methods for obtaining optically active 3-hydroxyhexanoic acids, (i) a method for increasing carbons stereoselectively of an enolate derived from optically active acylthiazolidinethione or acyloxazolidinethione by an aldol reaction, and cleaving the enolate by methanolysis (Hsiao et al., J. Org. Chem., 52, 2201 (1987)), (ii) a method for ring-opening an optically active epoxide derived from an optically active α-amino acid (Mori et al., Tetrahedron, 45, 1639 (1989)), (iii) a method of cyclization of an optically active hemiamidal in the presence of a mercury catalyst, separation of a resultant diasteleomer mixture, and hydrolysis of the compounds (Cardillo et al., J. Chem. Soc. Perkin Trans. 1, 1487 (1990)), (iv) a method of optical resolution of racemic 3-hydroxyhexanes by a hydrolysis or ester synthesizing reaction in the presence of lipase originating from Candida cylindracea (Engel et al., Enzyme Microb, Technol., 13, 655 (1991)), (v) a method for asymmetrically oxidizing a substrate such an hexanoic acid, 2-hexenoic acid and hexanol in the presence of Candida rugosa (Hasegawa et al., EP 0089039A2), (vi) a method for asymmetrically reducing a β-ketoester in the presence of Geotrichum candidum (Buisson et al., Biocatalysis, 5, 249 (1 992) and the like have been reported.

However, in method (i), since the amino acid leading an asymmetrical reaction as a starting material is used, it is relatively easy to obtain the S-compound of a natural type and it is difficult to obtain the R-compound of the antipode. Accordingly, in this method, only one of the optical isomers, the S-compound is sufficiently obtained. In method (ii), it is difficult to obtain the optically active α-amino acid of the starting material. Five troublesome steps are needed to obtain the product, and there are problems that the optical purity of the product is lowered (94% ee →76% ee) by racemization in the synthesis steps. In method (iii), there are problems of treatment of mercury which is used. It needs further unpractical column chromatography for separating diastereomer mixtures having low diastereo selectivity.

In method (iv), only products having low optical purity are obtained by either of hydrolysis and esterification. When racemic ethyl 3-acetoxyhexanoate is hydrolyzed into (S)-ethyl 3-hydroxyhexanoate, the resulting ester has low optical purity of 20% ee. In the reaction of racemic ethyl 3-hydroxyhexanoate and octanoic acid in an organic solvent, the reaction is troublesome due to esterification of the hydroxy group and acidolysis of the ethyl ester, and ethyl (S)-3-octanoyloxyhexanoate of the main product has unpreferable low optical purity (14% ee). In methods (v) and (vi), since the substrate concentration is low, i.e., 1% or less, it is necessary to use reaction and treatment equipment in large scale for mass production. The 3-hydroxyhexanoic acids obtained by these methods are only R-compounds and not S-compounds.

As described above, these conventional methods have unsatisfactory problems of industrial level operation;

SUMMARY OF THE INVENTION

The object of the present invention is to overcome the above problems of the prior arts, to provide a method for producing optically active 3-hydroxyhexanoic acids having high opticaly purity useful as intermediates for synthesizing medicine and agricultural chemicals in the high yield by simple operation.

To accomplish the above object, the present invention is as follows:

(1) A method for producing optically active 3-hydroxyhexanoic acids which comprises asymmetrically hydrolyzing a racemic ester of 3-hydroxyhexanoic acid represented by the following formula (1):

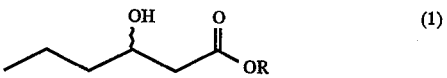

wherein R is straight or branched alkyl of 1–22 carbon atoms, alkenyl, cycloalkyl, aralkyl or aryl, in the presence of a porcine pancreas lipase, obtaining a mixture of (R)-3-hydroxyhexanoic acid represented by the following formula (2):

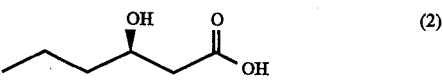

and an ester of (S)-3-hydroxyhexanoic acid represented by the following formula (3):

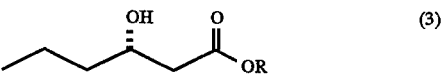

wherein R is as indicated above, and isolating these compounds as they are, or isolating both enantiomers after converting (R)-3-hydroxyhexanoic acid into a derivative of the carbonic acid.

(2) A method for producing (S)-3-hydroxyhexanoic acid represented by the following formula (4):

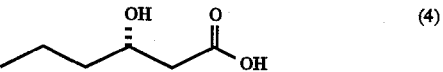

Which comprises further hydrolyzing the above ester of (S)-3-hydroxyhexanoic acid represented by the above formula (3) under acid or basic conditions.

(3) A method for producing optically active 3-hydroxyhexanoic acids as in (1), wherein the above asymmetrical hydrolyzing is conducted within the range of less than 50% conversion to obtain (R)-3-hydroxyhexanoic acid having high optical purity.

(4) A method for producing optically active 3-hydroxyhexanoic acids as in (1), wherein the above asymmetrical hydrolyzing is conducted within the range of more than 50% conversion to obtain an ester of (S)-3-hydroxyhexanoic acid having high optical purity.

Detailed Description of the Invention

In the method of the present invention, the racemic ester of 3-hydroxyhexanoic acid represented by the formula (1) is used as a starting material, wherein R is selected from straight or branched alkyl of 1–22 carbon atoms, alkenyl, cycloalkyl, aryl or aralkyl.

As preferable examples of R of the above formulas, methyl, ethyl, n-propyl, n-butyl and n-pentyl in case of straight chain alkyl; i-propyl, sec-butyl, t-butyl and neopentyl in case of branched chain alkyl; vinyl and 2-methyl vinyl in case of alkenyl; cyclohexyl in case of cycloalkyl; phenyl in case of aryl; and benzyl in case of aralkyl can be exemplified, respectively.

The ester of racemic 3-hydroxyhexanoic acid represented by the formula (1) is obtained by reducing an easily available ester of 3-ketohexanoic acid such as methyl 3-ketohexanoate or ethyl 3-ketohexanoate by using a well-known method, and if necessary converting the alkoxy group in the ester into the preferable alkoxy group by using a well-known method.

As the process for reducing the ester, catalytic hydrogenation, reduction by using a hydrogenated metal compound or the like can be exemplified. As the catalyst of the catalytic hydrogenation, Raney nickel, palladium carbon and platinum black can be exemplified. As the hydrogenated metal, sodium borohydride and lithium aluminum hydride can be exemplified.

As the method for conversion of the alkoxy group in the ester into a preferable alkoxy group, for example, there is a method of transesterification of the alkoxy group in a desired alcohol in the presence of an acid catalyst, or a method of re-esterification of a carboxylic acid, which is obtained by hydrolysis of the ester, by reacting with a halogenated alkyl in the presence of a base.

Essentials of the method for producing an optically active compound in the present invention comprise stirring a racemic ester of 3-hydroxyhexanoic acid represented by formula (1) in the presence of a lipase derived from porcine pancreas with solvent to hydrolyze the ester.

The reaction temperatures of the hydrolyzing step are suitably 0° C. to 100° C., preferably 10° C. to 50° C.

The reaction times are suitably 1 to 1000 hours, preferably 1 to 200 hours. Namely, the reaction time depends on the kind of the racemic esters of 3-hydroxy hexanoic acid which are starting materials. The conversion of 20–80% is attained within the above preferable reaction times. In this case, in the reaction of the conversion of 50% or less, (R)-3-hydroxyhexanoic acid having optical purity over 90% ee is obtained, while in the reaction of the conversion of 50% or more, (S)-3-hydroxyhexanoic acid having optical purity over 90% ee is obtained.

As the lipase derived from porcine pancreas, Lipase type II (trade name, manufactured by Sigma Chemical Co. , Ltd.), Lpase (pancreas, trade name, manufactured by Tokyo Kasei Co., Ltd.) can be exemplified.

The amount of the Lipase used is generally suitable at 0.1 to 1000% by weight of the substrate, preferably 1 to 200% by weight.

As the solvent used, ion exchange water, distilled water or buffer liquid is suitable. Organic solvent having good solubility with these solvents, such as acetone, N,N-dimethyl formamide, dimethyl sulfoxide, alcohol and the like can be used as a co-solvent. The amount of the solvent is 0.1 to 100 times by weight, preferably 1 to 10 times by weight of the racemic ester of 3-hydroxyhexanoic acid of the substrate.

After the hydrolyzing reaction, the mixture of esters of (R)-3-hydroxyhexanoic acid and (S)-3-hydroxyhexanoic acid can be obtained. Although the mixture can be separated as it is, for easy separation, it is possible to convert (R)-3-hydroxyhexanoic acid into an ester of the carboxylic acid and to separate both the enantiomers. As an embodiment method for obtaining derivatives of the carboxylic acid, an esterification method of methylesterification using diazomethane can be exemplified. The separation of S-and R-compound mixtures can be conducted by distillation, column chromatography or the like.

After (R)-3-hydroxyhexanoic acid or the derivative and ester of (S)-3-hydroxyhexanoic acid are separated, the latter ester is hydrolyzed under acid or basic conditions to obtain (S)-3-hydroxyhexanoic acid. In the former, the derivative of (R)-3-hydroxyhexanoic acid is hydrolyzed under acid or basic conditions to obtain (R)-3-hydroxyhexanoic acid.

The optically active 3-hydroxyhexanoic acids are useful as intermediates for synthesizing medicines and agricultural chemicals.

As an example, monocerine (6) useful as an insecticide or antibiotic agent is obtained from (S)-3-hydroxyhexanoic acid (4) via (S)-ethyl 3-hydroxyhexanoate (5) as shown in the following (Mori et al; Tetrahedron, 45, 1639 (1989):

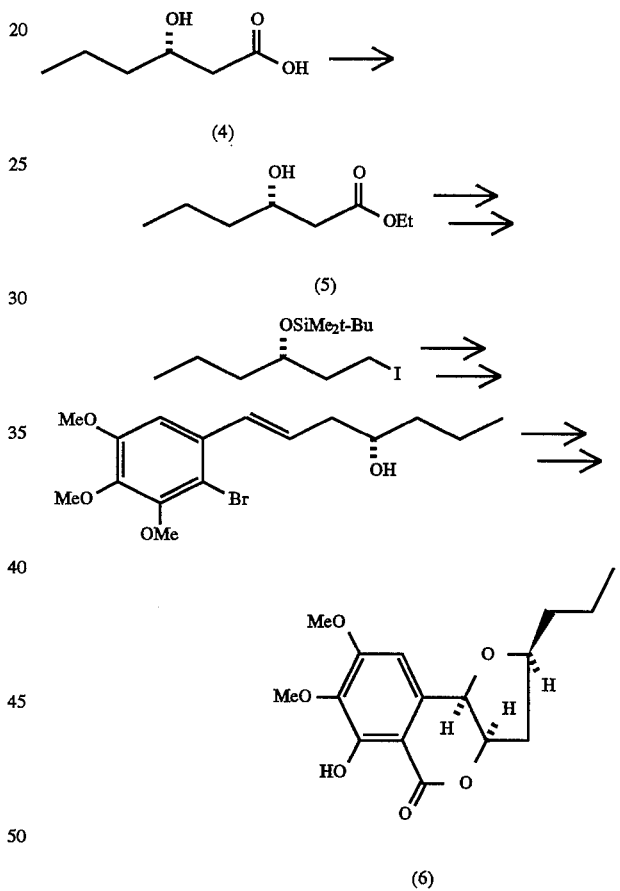

The merits of the present invention are as follows:

(1) Enantiomers of the optically active esters of 3-hydroxyhexanoic acid having high optical purity can be obtained; R-compounds of 91% ee and Z-compounds of 97% ee.

(2) By using a hydrolyzing reaction, an open system can be used without taking care that water is present.

(3) The reaction can be conducted under mild conditions, such as at room temperature.

(4) The object products can be easily mass-produced by few steps.

(5) By controlling the conversion, it is possible to obtain preferably a R- or S-enantiomer having high optical purity.

DESCRIPTION OF THE PREFERRED EMBODIMENTS

The following examples illustrate the present invention more specifically, but these are not intended as a definition of the limits of the invention.

The optical purity of optically active esters of 3-hydroxyhexanoic acid in the examples was determined by the following method: an ester of 3-hydroxyhexanoic acid was reacted with 2, 4-dinitro phenylisocyanate in dichloromethane to convert into a corresponding urethane derivative. The derivative was analyzed by HPLC (the column used: trade name of Sumikiral OA 3000, manufactured by Sumitomo Analytical Center; developed solvent: hexane/dichloroethane/ethanol=100/20/1) to determine the optical purity.

REFERENCE EXAMPLE 1

Synthsis of racemic ethyl 3-hydroxyhexanoate

Ethyl 3-ketohexanoate 50 g (0.32 mol), Raney nickel 10 g and tetrahydrofuran 500 ml were mixed, and the mixture was reacted with stirring in an autoclave at a temperature of 50° C. and a hydrogen pressure of 5 kg/cm$^2$ for 30 hours. After removing the Raney nickel from the reactant by filtration, the filtrate was concentrated and distilled under reduced pressure to obtain racemic ethyl 3-hydroxyhexanoate 42 g ( 0.26 mol, 85%).

REFERENCE EXAMPLE 2

Synthesis of racemic butyl 3-hydroxyhexanoate

The racemic ethyl 3-hydroxyhexanoate 40 g (0.25 mmol) obtained in Reference example 1, hydrated p-toluenesulfonic acid 2.4 g and n-butanol 190 ml were mixed, and the mixture was reacted with stirring in a stream of nitrogen at 75° C. for 15 hours. After cooling, the reactant was neutralized with an aqueous solution of saturated sodium bicarbonate. The solution was extracted with ethyl acetate, the organic phase was washed with a saturated aqueous solution of sodium chloride and dried over anhydrous magnesium sulfate, and the solvent was distilled off under reduced pressure. The residue was distilled under reduced pressure to obtain racemic butyl 3-hydroxyhexanoate 42 g (0.22 mol, 93%).

REFERENCE EXAMPLE 3

Synthesis of racemic benzyl 3-hydroxyhexanoate

The racemic ethyl 3-hydroxyhexanoate 3.46 g (21.6 mmol) obtained in Reference example 1 was dissolved in methanol 24 ml, sodium hydroxide 0.95 g in water 24 ml was added dropwise with cooling, and the mixture was reacted with stirring in a stream of nitrogen at room temperature for two hours. Methanol was removed from the reactant under reduced pressure, and the residue was neutralized with 1N-HCl. After saturating the resultant by adding sodium chloride, the solution was extracted with ethyl acetate, the extract was dried over anhydrous magnesium sulfate and the solvent was distilled off under reduced pressure to obtain racemic 3-hydroxyhexanoic acid 2.50 g (18.9 mmol, 87%). The resultant, benzyl bromide 6.47 g (37.8 mmol). sodium bicarbonate 3,81 g (45.4 mmol) and N,N-dimethylformamide 20 ml were reacted with stirring at room temperature for 27 hours in a stream of nitrogen. The reaction mixture was extracted with ethyl acetate, and the extract was dried over anhydrous magnesium sulfate and filtered, and the solvent was distilled off under reduced pressure. The residue was chromatographed with silica gel column to obtain racemic benzyl 3-hydroxyhexanoate 2.11 g (9.5 mmol, 50%).

Example 1

The racemic butyl 3-hydroxyhexanoate 1.0 g (5.3 mmol) obtained in Reference example 2, lipase 0.2 g (Lipase type II, manufactured by Sigma Chemical Co., Ltd.) and a 0.7M phosphate buffer solution (pH 7.0) 10 ml were mixed and reacted with stirring at room temperature for 22 hours. After the reaction was stopped, the conversion of the above racemic compound was 38%. After removing the lipase from the reactant by filtration, the filtrate was extracted with diethyl ether and the extract was dried over anhydrous magnesium sulfate.

To convert (R)-3-hydroxyhexanoic acid produced by the above hydrolyzing into a methyl ester, the extract was treated with diazomethane and the solvent was distilled off under reduced pressure. The residue was chromatographed with a silica gel column to obtain (R)-methyl 3-hydroxyhexanoate 0.23 g (1.2 mmol, 23%) and (S)-butyl 3-hydroxyhexanoate 0.56 g (3.0 mmol, 56%). These compounds were treated with HPLC to determine the optical purity. The optical purity of the (R)-compound was 91% ee and that of the (S)-compound was 56% ee.

Example 2

The same procedure was repeated as in Example 1 except that the amount of the lipase was changed into 1.0 g and the stirring time was changed into 25 hours. After stirring the mixture, the reaction was stopped and the conversion of 58% was determined. The steps from the filtration of the lipase to chromatograph with a silica gel column were conducted as shown in Example 1 to obtain (R)-methyl 3-hydroxyhexanoate 0.25 g (1.7 mmol, 32%) and (S)-butyl 3-hydroxyhexanoate 0.29 g (1.5 mmol, 29%). Optical purity of the compounds was determined by HPLC. The optical purity of the R-compound was 70% ee and that of the S-compound was 97% ee.

Comparative Examples 1–6

Given amounts of several kinds of lipases as shown in Table 1, racemic butyl 3-hydroxyhexanoate 1.0 g (5.3 mmol) and a 0.7M phosphate buffer solution (pH 7.0) 10 ml were mixed and stirred at room temperature for given hours. The results of the conversion and the optical purity were shown in Table 1.

TABLE 1

| Comparative examples | Lipase (trade name) (g) | Reaction time (hr) | Conversion (%) | Optical purity (ee %) R– | Optical purity (ee %) S– |
|---|---|---|---|---|---|
| 1 | SP435*[1] 0.05 | 1 | 44 | 72 | 57 |
| 2 | SP435*[1] 0.2 | 2.5 | 62 | 50 | 82 |
| 3 | Lipozyme™*[2] 0.2 | 24 | 37 | 12 | 7 |
| 4 | Lipase type VII*[3] 0.2 | 140 | 33 | 59 | 29 |
| 5 | Asahi Chemical's Lipase*[4] 0.2 | 8 | 44 | 62 | 49 |
| 6 | Toyobo Lipase*[5] 0.2 | 26 | 38 | 55 | 34 |

*[1]: Origin/*Candida antarctica*, manufactured by Novo Nordisk
*[2]: Origin/*Mucoi miehei*, manufactured by Novo Nordisk
*[3]: Origin/*Candida cylindracea*, manufactured by Sigma Chemical Co., Ltd.
*[4]: Origin/*Chromobacterium viscosum*, manufactured by Asahi Chmical Industry Co., Ltd.
*[5]: Origin/Pseudomonas SP., manufactured by Toyobo Co., Ltd.

As shown in Examples 1 and 2, the preferable isomers of the R-compound and the S-compound having high optical purity (91–97% ee) can be obtained by using a porcine pancreas lipase and by adjusting the conversion rate. On the other hand, in Comparative examples 1–6, even if other lipases were used, it is possible to obtain the R-compound having optical purity only 12–72% ee and the S-compound having purity of only 7–82% ee of 3-hydroxyhexanoic acids. It appears that the optical purity of the compounds of Comparative examples is less than that of the Examples.

Example 3

The same procedure was repeated except that racemic butyl 3-hydroxyhexanoate was changed into the racemic benzyl 3-hydroxyhexanoate 1.0 g (4.5 mmol) obtained in Reference example 3 and stirring time was changed into nine hours. The resulting mixture was reacted with stirring. After the reaction was stopped, the conversion of 52% was determined. The steps from filtration of the lipase to chromatograph with a silica gel column were conducted as shown in Example 1 to obtain (R)-methyl 3-hydroxyhexanoate 0.24 g (1.6 mmol, 36%) and (S)-benzyl 3-hydroxyhexanoate 0.40 g (1.8 mmol, 40%). Optical purity of these compounds was determined by HPLC. The optical purity of the (R)-compound was 88% ee and that of the (S)-compound was 96% ee.

Comparative Examples 7 and 8

0.2 g of two kinds of lipases as shown in Table 2, racemic benzyl 3-hydroxyhexanoate 1.0 g (4.5 mmol) and 0.7M phosphate buffer solution (pH 7.0) 10 ml were mixed and stirred at room temperature for given hours. The results of the conversion and the optical purity were shown in Table 2.

TABLE 2

| Comparative examples | Lipase (trade name) (g) | Reaction time (hr) | Conversion (%) | Optical purity (ee %) R– | Optical purity (ee %) S– |
|---|---|---|---|---|---|
| 7 | SP435*1 0.2 | 2.3 | 80 | 9 | 37 |
| 8 | Asahi Chemical's Lipase*2 0.2 | 3.3 | 53 | 63 | 72 |

*1: Origin/*Candida antarctica*, manufactured by Novo Nordisk.
*2: Origin/*Chromobacterium viscosum*, manufactured by Asahi Chemical Industry Co.,Ltd.

As shown in Example 3, it is possible to obtain optical isomers having high optical purity (R-compound: 88% ee, S-compound: 96% ee) by using a porcine pancreas lipase. On the other hand, in Comparative examples 7 and 8, although the reaction rate is high, the stereoselectivity is low. The optical purity of resulting 3-hydroxyhexanoic acids was 9–63% ee in case of the R-compound and it was 37–72% ee in case of the S-compound. It appears that the optical purity of the compounds of Comparative examples is less than that of the Examples.

We claim:

1. A method for producing optically active 3-hydroxy-hexanoic acid comprising:

asymmetrically hydrolyzing a racemic ester of 3-hydroxy-hexanoic acid of formula (1)

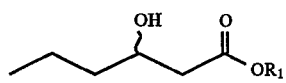

wherein $R_1$ is butyl or benzyl, with a conversion of less than 50%, with a porcine pancreatic lipase, obtaining (R)-3-hydroxy-hexanoic acid of formula (2) with an optical purity of over 90%

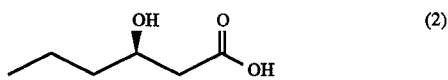

and an ester of (S)-hydroxy-hexanoic acid of formula (3) wherein $R_1$ is the same as above

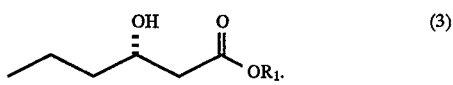

2. The method of claim 1 further comprising hydrolyzing the ester of (S)-3-hydroxy-hexanoic acid of formula (3) under acid or basic conditions to obtain (S)-3-hydroxy-hexanoic acid of formula (4)

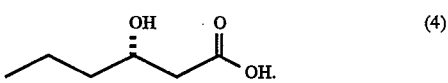

3. The method of claim 1 further comprising converting the (R)-3-hydroxy-hexanoic acid of formula (2) into an ester.

4. A method for producing optically active 3-hydroxy-hexanoic acid comprising:

asymmetrically hydrolyzing a racemic ester of 3-hydroxy-hexanoic acid of formula (1)

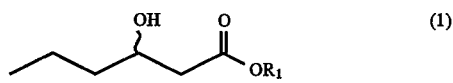

wherein $R_1$ is butyl or benzyl, with a conversion of greater than 50%, with a porcine pancreatic lipase, obtaining (R)-3-hydroxy-hexanoic acid of formula (2)

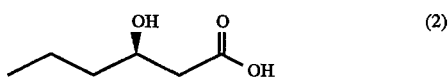

and an ester of (S)-3-hydroxy-hexanoic acid of formula (3) with an optical purity of over 90% wherein $R_1$ is the same as above

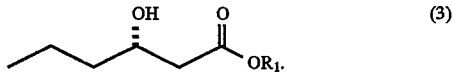

5. The method of claim 4 further comprising hydrolyzing the ester of (S)-3-hydroxy-hexanoic acid of formula (3) under acid or basic conditions to obtain (S)-3-hydroxy-hexanoic acid of formula (4)

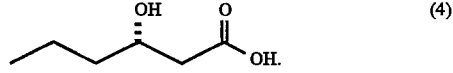

6. The method of claim 1 further comprising converting the (R)-3-hydroxy-hexanoic acid of formula (2) into an ester and isolating the compounds.

* * * * *